(12) United States Patent
Chen et al.

(10) Patent No.: US 7,016,029 B2
(45) Date of Patent: Mar. 21, 2006

(54) DETECTION OF LENS ANTI-REFLECTIVE COATING DECAY BY UNDESIRED RESIDUE DETECTION

(75) Inventors: Hung-Chih Chen, Hsin Chu (TW); Chao-Hsiung Wang, Taipei (TW); Niahn-Mauh Shih, Miaoli (TW); Hsien-Wei Chin, Hsin Chu (TW)

(73) Assignee: Taiwan Semiconductor Manufacturing Co., Ltd., Hsin Chu (TW)

( * ) Notice: Subject to any disclaimer, the term of this patent is extended or adjusted under 35 U.S.C. 154(b) by 764 days.

(21) Appl. No.: 10/167,162

(22) Filed: Jun. 11, 2002

(65) Prior Publication Data

US 2003/0228531 A1 Dec. 11, 2003

(51) Int. Cl.
*G01N 21/00* (2006.01)
(52) U.S. Cl. .................................. 356/237.2; 356/446
(58) Field of Classification Search ............. 356/237.1, 356/237.2
See application file for complete search history.

(56) References Cited

U.S. PATENT DOCUMENTS 5,825,486 A * 10/1998 Zavislan et al. ............ 356/326

* cited by examiner

*Primary Examiner*—Layla G. Lauchman
*Assistant Examiner*—Juan D. Valentin, II
(74) *Attorney, Agent, or Firm*—Tung & Assoc.

(57) ABSTRACT

Detecting decay of equipment lens anti-reflective coating (ARC) by detecting undesired residue is disclosed. The undesired residue detected correlates with the decay of the ARC, where a greater amount of undesired residue detected indicates a greater level of the decay. The undesired residue is detected due to stray light reflected by the ARC because of its decay. In the context of semiconductor fabrication equipment, photoresist residue results from negative photoresist on a semiconductor wafer, and may be viewed on one or more scribe lines of a mask within a field of view of the lens of the semiconductor fabrication equipment.

20 Claims, 4 Drawing Sheets

DETECTION OF LENS ANTI-REFLECTIVE COATING DECAY BY UNDESIRED RESIDUE DETECTION

FIELD OF THE INVENTION

This invention relates generally to equipment that have lenses with anti-reflective coatings (ARC's), such as semiconductor equipment having such lenses, and more particularly to detecting decay of the ARC's of the lenses of such equipment.

BACKGROUND OF THE INVENTION

Since the invention of the integrated circuit (IC), semiconductor chip features have become exponentially smaller and the number of transistors per device exponentially larger. For example, advanced IC's with hundreds of millions of transistors at feature sizes of 0.25 micron, 0.18 micron, and less are becoming routine. Improvement in overlay tolerances in photolithography, and the introduction of new light sources with progressively shorter wavelengths, have allowed optical steppers to significantly reduce the resolution limit for semiconductor fabrication far beyond one micron. To continue to make chip features smaller, and increase the transistor density of semiconductor devices, IC's have begun to be manufactured that have features smaller than the lithographic wavelength.

Sub-wavelength lithography, however, places large burdens on lithographic processes. Resolution of anything smaller than a wavelength is generally quite difficult. Pattern fidelity can deteriorate dramatically in sub-wavelength lithography. The resulting semiconductor features may deviate significantly in size and shape from the ideal pattern drawn by the circuit designer. Critical dimensions (CD's), which are the geometries and spacings used to monitor the pattern size and ensure that it is within the customer's specification, are especially important to have size maintenance during processing. CD non-uniformity refers to when the designed and actual values do not match, or when the CD's of multiple features on the same semiconductor device that should be identical are not. Ideally, CD non-uniformity is minimized, but in actuality such non-uniformity can measurably affect the resulting semiconductor device's performance and operation.

One cause of CD non-uniformity is the decay of the anti-reflective coating's (ARC's) around the sidewalls of the lenses of semiconductor equipment. Such semiconductor equipment can include steppers and scanners. Steppers and scanners are types of semiconductor fabrication equipment used in photolithographic processing, such as aligning a mask over a wafer and exposing the pattern of the mask onto the wafer. A scanner typically uses a mirror system with a slit blocking part of the light coming from the light source. The size of the slit is smaller than the wafer, so the light beam scans across the wafer. Whereas scanning is generally performed on a per-wafer basis, a stepper is utilized on only a given part of the wafer at one time. A reticle is aligned and exposed, without scanning, and then is stepped to the next site and the process is repeated. Stepping generally allows more precise matching of larger-diameter wafers than scanners do.

Another type of semiconductor fabrication equipment combines the stepping and scanning process of steppers and scanners, and is known as step and scan aligners. At one position on the semiconductor wafer, a small-scale scanning process takes place, and then the reticle or mask is stepped to the next position, where the scanning process is repeated. As used herein, steppers, scanners, and step and scan aligners are generally encompassed under the term alignment and exposure equipment, which can include other types of specific semiconductor fabrication equipment besides steppers, scanners, and step and scan aligners. Furthermore, unless otherwise and specifically noted, steppers, scanners, and step and scan aligners are used substantially interchangeably herein, such that reference to or description of one should be assumed to apply to other types of alignment and exposure equipment as well.

The ARC of the lens of such a semiconductor equipment reduces the scattering effects of the light that reflects from the sidewalls of the lens. The ARC is a thin film placed on the outside of the sidewalls of the lens. Where the ARC has not decayed, little or no light is reflected back from the sidewalls. This is shown in FIG. 1. The stepper system 100 includes one or more lenses 102 through which light passes through after first passing through a mask or a reticle 104. The lenses 102 aim the light onto the wafer 110 sitting on the stage 108, as indicated by the aimed light beams 106. In FIG. 1, the lenses 102 have an ARC on their circumferential sidewalls that prevents light from reflecting back from the sidewalls, where the sidewalls are the vertical edges of the lenses 102, and not the top or the bottom of the lenses 102. However, where the ARC has decayed, the light reflects off the sidewalls, causing scattered light to reach the wafer 110 in addition to the aimed light beams 106, which can cause CD non-uniformity.

Unfortunately, currently there is no manner by which to measure or detect the extent to which the ARC's of semiconductor equipment lenses have decayed. This can cause significant wafer scrap, because the CD's of many wafers may be fabricated non-uniformly before they are discovered. Wafer scrap can sometimes be reused, but often is discarded, resulting in added costs incurred by the semiconductor foundry. Manual inspection of semiconductor equipment for lens ARC decay is time-consuming, and also expensive. Therefore, there is a need for detecting the decay of ARC's of semiconductor equipment lenses. More specifically, there is a need for measuring the extent of such decay. For these and other reasons, there is a need for the present invention.

SUMMARY OF THE INVENTION

The invention relates to detecting decay of equipment lens anti-reflective coating (ARC) by detecting undesired residue. The undesired residue detected correlates with the decay of the ARC, where a greater amount of undesired residue detected indicates a greater level of the decay. The undesired residue is detected due to stray light reflected by the ARC because of its decay. In the context of semiconductor fabrication equipment, preferably the undesired residue results from negative photoresist on a semiconductor wafer, and is viewable on one or more scribe lines of a mask within a field of view of the lens of the semiconductor fabrication equipment.

Embodiments of the invention provide for advantages over the prior art. In the context of semiconductor fabrication equipment, the presence of the photoresist residue indicates decay of the ARC of the lens of the semiconductor fabrication equipment. Measuring the photoresist residue thus is indicative of the extent to which the ARC has decayed. By knowing when the ARC has decayed past a desired level, significant semiconductor scrap can be avoid. Still other advantages, aspects, and embodiments of the invention will become apparent by reading the detailed description that follows, and by referring to the accompanying drawings.

DETAILED DESCRIPTION OF THE INVENTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims. For example, whereas the invention is substantially described in relation to semiconductor fabrication equipment, it is applicable to other types of equipment as well, such as opto-electronic devices, superconductor devices, micro-machine devices, bio-chip devices, and so on.

Figure 1:
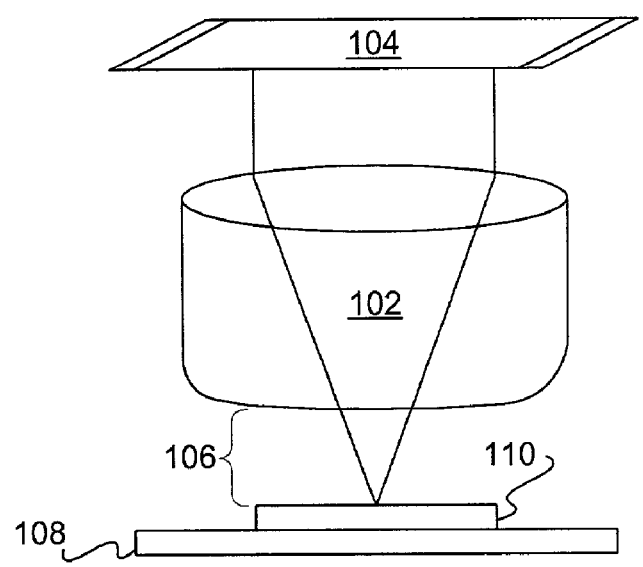
FIG. 1 is a diagram showing a representative semiconductor fabrication photolithographic equipment, such as a scanner or a stepper, that can be used in conjunction with embodiments of the invention.
Figure 1:
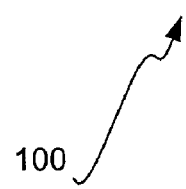
Figure 2:
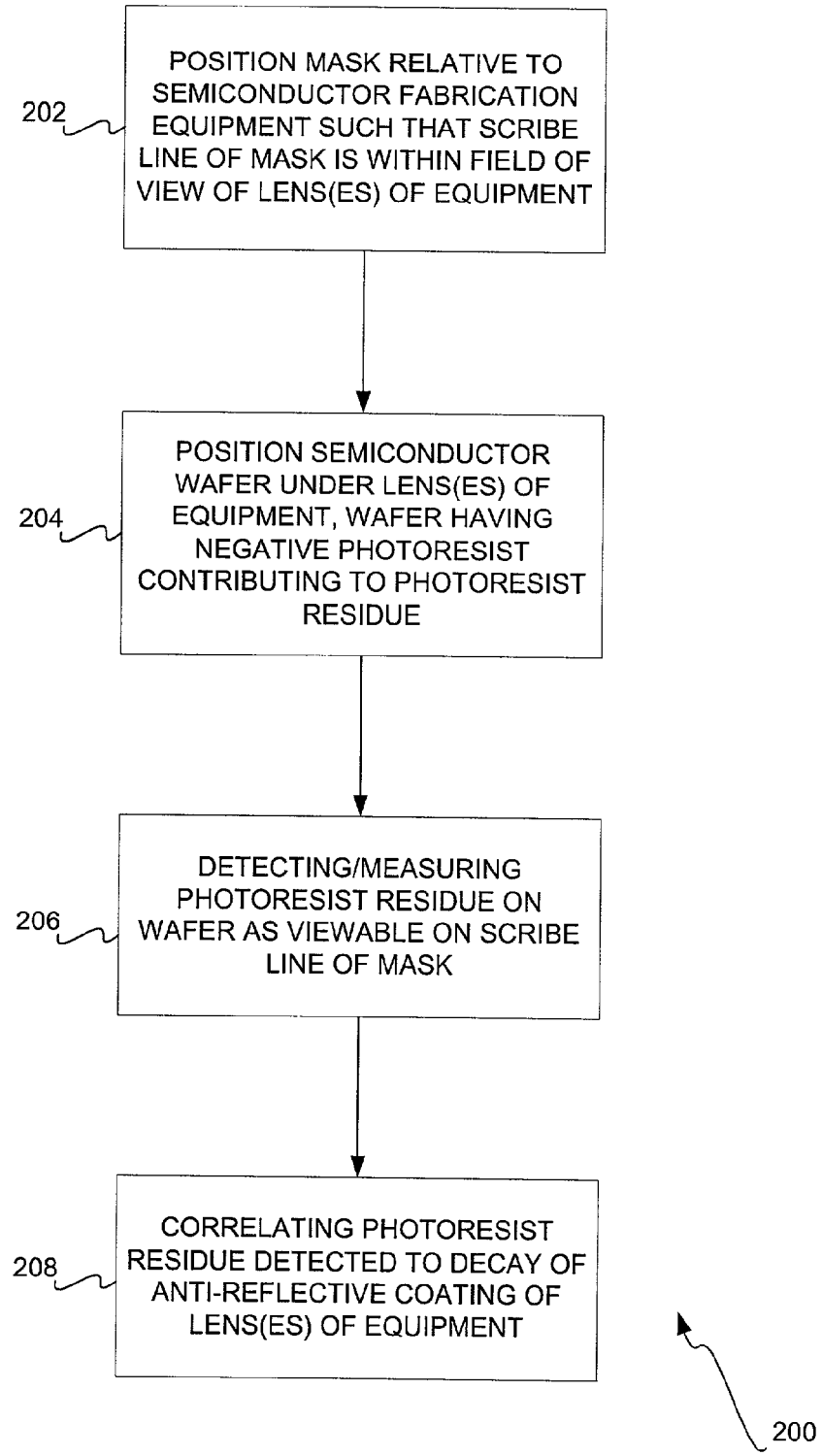
FIG. 2 is a flowchart of a method according to an embodiment of the invention for detecting decay and/or measuring the extent of the decay of an anti-reflective coating (ARC) of a semiconductor fabrication equipment lens.

FIG. 2 shows a method 200 according to an embodiment of the invention. The method 200 can be performed, and other embodiments of the invention can be implemented, in conjunction with semiconductor fabrication equipment. The equipment may be a stepper, a scanner, or another type of photolithographic or other semiconductor fabrication equipment or equipment assembly. For example, the equipment may be the equipment of FIG. 1 that has been described. Therefore, for instance, reference of the description of the method 200 to semiconductor fabrication equipment can in one embodiment imply reference to the equipment of FIG. 1.

Figure 3:
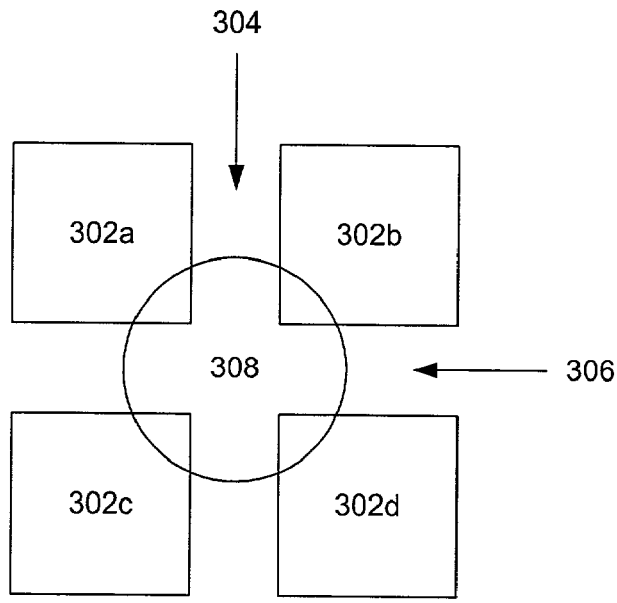
FIG. 3 is a diagram of an example mask that can be used in one embodiment of the invention in conjunction with the method of FIG. 2.

First, a mask is positioned over one or more lenses of the semiconductor fabrication equipment (202). The mask preferably has an m die-by-n die pattern or configuration, or an n die-by-n die pattern or configuration, where m and n are at least greater than one, and preferably even. FIG. 3 shows an example of such a mask 300 that can be used. The mask 300 has die areas 302a, 302b, 302c, and 302d arranged in a two die-by-two die pattern or configuration. Scribe lines 304 and 306 separate the die areas 302a, 302b, 302c, and 302d. The mask 300 is preferably positioned over the one or more lenses such that the intersection of the scribe lines 304 and 306 is centered within a field of view 308 of the one or more lenses. Alternatively, the mask 300 is positioned over the one or more lenses such that one or more parts of the scribe lines 304 and 306 is viewable within the field of view 308 of the one or more lenses.

Figure 4:
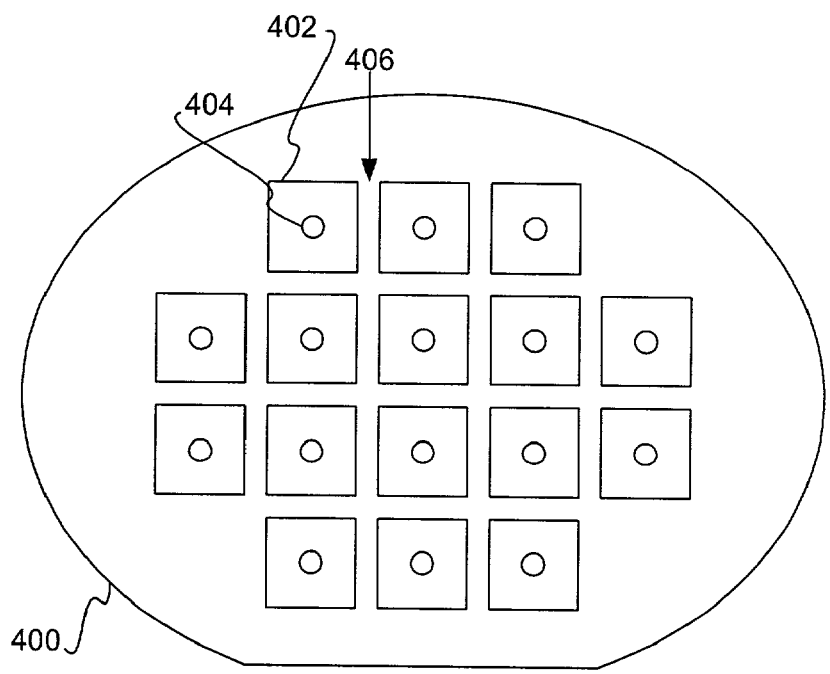
FIG. 4 is a diagram of an example semiconductor wafer that can be used in one embodiment of the invention in conjunction with the method of FIG. 2.
Figure 5:
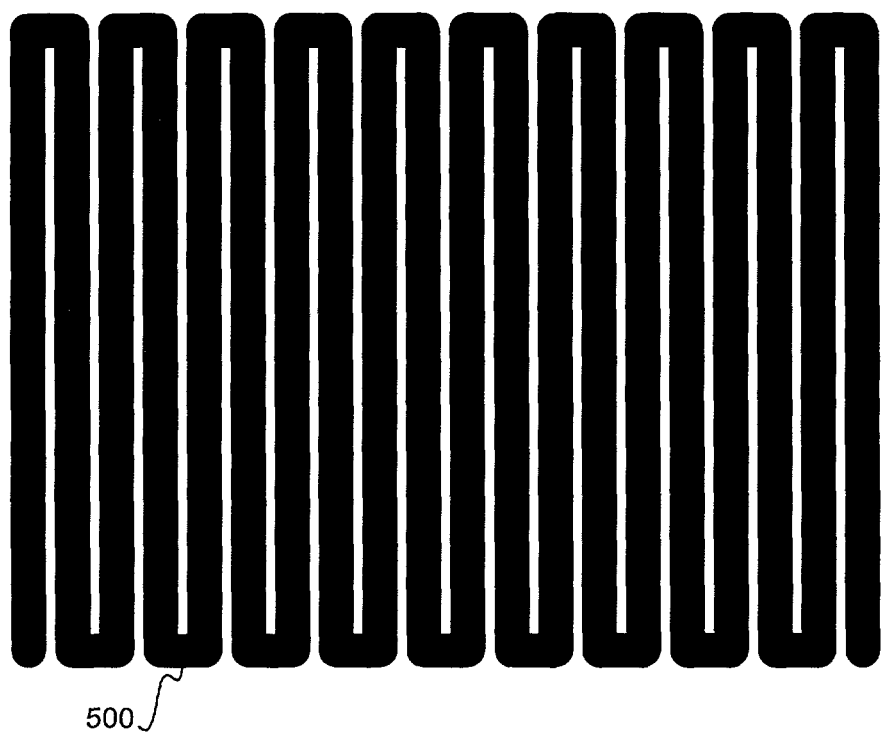
FIG. 5 is a diagram of an example meandering pattern that can be used in one embodiment of the invention on the semiconductor wafer of FIG. 4.

Referring back to FIG. 2, a semiconductor wafer is then positioned under the one or more lenses of the semiconductor fabrication equipment (204). The semiconductor wafer has negative photoresist, which contributes the photoresist residue to be detected as viewable on the scribe line of the mask. FIG. 4 shows an example of such a semiconductor wafer 400 that can be used. The mask 400 has a number of dies, such as the semiconductor die 402, separated by scribe lines, such as the scribe line 406. The field of view of the one or more lenses of the semiconductor fabrication equipment can be positioned over the centers of the dies, as indicated by the circles within the dies of the mask 400, such as the circle 404. It is noted that the mask previously positioned over the lenses of the equipment has its scribe lines positioned within the field of view, such that in at least one embodiment, the scribe lines of the mask do not line up with the scribe lines of the wafer. The wafer also preferably has a meandering pattern. An example of a meandering pattern is shown in FIG. 5 as the pattern 500.

Referring back to FIG. 2, the photoresist residue on the semiconductor wafer, as viewable on the scribe line of the mask, is next detected or measured (206). The photoresist residue detected results from stray light reflected by an anti-reflective coating (ARC), where the ARC has decayed. That is, the decay of the ARC of the lenses of the semiconductor fabrication equipment causes stray light to be reflected by the ARC, which allows for the photoresist residue as viewable on the scribe line of the mask to be detected through the field of view of the lenses of the semiconductor fabrication equipment.

Figure 6:
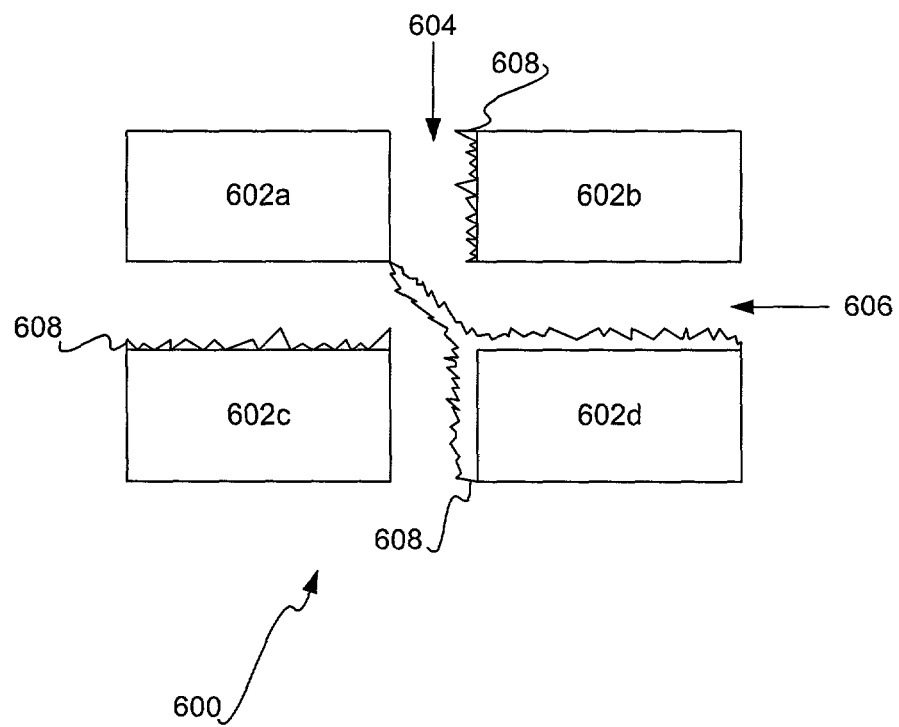
FIG. 6 is a diagram showing, as an example, photoresist residue on a semiconductor wafer as viewable on the scribe line of a mask through the field of view of the lens of semiconductor fabrication equipment having a decayed ARC, according to an embodiment of the invention.

FIG. 6 shows an example of such photoresist residue on the semiconductor wafer as viewable on the scribe line of the mask through the lens of the semiconductor fabrication equipment. The field of view 600 can correspond to the field of view 308 of FIG. 3. Within the field of view 600 are shown parts of dies 602a, 602b, 602c, and 602d, which can correspond to the dies 302a, 302b, 302c, and 302d of FIG. 3. The scribe lines 604 and 606 separate the dies 602a, 602b, 602c, and 602d, and can correspond to the scribe lines 304 and 306 of FIG. 3. Within the scribe lines 304 and 306 is viewable, detectable, and measurable, photoresist residue 608 on the semiconductor wafer, such as the wafer 400 of FIG. 4.

Therefore, referring back to FIG. 2, the photoresist residue that has been detected or measured is correlated to the decay of the ARC of the lens of the semiconductor fabrication equipment (208). The greater the amount of the residue detected, the greater the extent or level to which the ARC of the lens has decayed. Similarly, the lesser the amount of the residue detected, the lesser the extent or level to which the ARC of the lens has decayed.

It is noted that, although specific embodiments have been illustrated and described herein, it will be appreciated by those of ordinary skill in the art that any arrangement is calculated to achieve the same purpose may be substituted for the specific embodiments shown. This application is intended to cover any adaptations or variations of the present invention. For example, whereas the invention is substantially described in relation to semiconductor fabrication equipment, it is applicable to other types of equipment as well, such as opto-electronic devices, superconductor devices, micro-machine devices, bio-chip devices, and so on.

Furthermore, whereas photoresist residue has been indicated as the undesired residue detected on the lenses, other types of undesired residues may also be present on a substrate. The substrate specifically has been described as a semiconductor wafer, but may be another type of substrate, such as an oxide, an alloy, and so on. Therefore, it is manifestly intended that this invention be limited only by the claims and equivalents thereof.

What is claimed is:

1. A method comprising:
    detecting undesired residue on a substrate using equipment having one or more lenses with an anti-reflective coating; and,
    correlating decay of the anti-reflective coating of the one or more lenses of the equipment to the undesired residue detected on the substrate, wherein a greater amount of the undesired residue detected indicating a greater level of the decay of the anti-reflective coating of the one or more lenses of the fabrication equipment.

2. The method of claim 1, wherein the undesired residue comprises photoresist residue, the equipment comprises semiconductor fabrication equipment, and the substrate comprises a semiconductor wafer.

3. The method of claim 2, further initially comprising positioning a mask over the one or more lenses and the semiconductor wafer, the mask having a scribe line at a center of a field of view where the photoresist residue is to be detected.

4. The method of claim 2, further initially comprising positioning the semiconductor wafer under the one or more lenses, the semiconductor wafer having a negative photoresist that contributes the photoresist residue to be detected.

5. The method of claim 2, wherein the photoresist residue detected results from stray light reflected by the anti-reflective coating as a result of the decay of the anti-reflective coating.

6. The method of claim 2, wherein detecting the photoresist residue comprises using a mask in conjunction with the semiconductor fabrication equipment having a scribe line in a center of a field of view of the one or more lenses.

7. The method of claim 2, wherein detecting the photoresist residue comprises measuring the photoresist residue.

8. The method of claim 2, wherein the semiconductor fabrication equipment is photolithographic equipment.

9. The method of claim 2, wherein the semiconductor fabrication equipment is one or more of a stepper and a scanner.

10. A semiconductor fabrication equipment assembly comprising:
    one or more lenses having a field of view;
    an anti-reflective coating on a sidewall of the one or more lenses and having decay;
    a mask positioned relative the one or more lenses such that a scribe line of the mask is in the field of view;
    stage; and,
    a semiconductor wafer placed on the stage, positioned under the one or more lenses, and having a negative photoresist, such that photoresist residue contributed by the negative photoresist and detectable on the scribe line of the mask through the one or more lenses correlates to the decay of the anti-reflective coating.

11. The assembly of claim 10, wherein a greater amount of the photoresist residue detectable indicates a greater level of the decay of the anti-reflective coating.

12. The assembly of claim 10, wherein the photoresist residue detectable results from stray light reflected by the anti-reflective coating as a result of the decay of the anti-reflective coating.

13. The assembly of claim 10, wherein the mask has an m die-by-n die pattern, where m and n are greater than one.

14. The assembly of claim 10, wherein the mask has an n die-by-n die pattern, where n is greater than one.

15. The assembly of claim 10, wherein the mask has an n die-by-n die pattern, where n is an even number.

16. The assembly of claim 10, wherein the assembly is a photolithographic equipment assembly.

17. The assembly of claim 10, wherein the assembly is one of a stepper assembly and a scanner assembly.

18. A method comprising:
    positioning a mask over one or more lenses of semiconductor fabrication equipment, the mask having a scribe line within a field of view of the one or more lenses;
    positioning a semiconductor wafer under the one or more lenses of the semiconductor fabrication equipment, the semiconductor wafer having a negative photoresist that contributes photoresist residue viewable on the scribe line of the mask;
    detecting photoresist residue on the semiconductor wafer as viewable on the scribe line of the mask, the photoresist residue detected resulting from stray light reflected by an anti-reflective coating of the one or more lenses as a result of decay of the anti-reflective coating; and,
    correlating decay of the anti-reflective coating of the one or more lenses of the semiconductor fabrication equipment to the photoresist residue detected on the semiconductor wafer as viewable on the scribe line of the mask.

19. The method of claim 18, wherein a greater amount of the photoresist residue detected indicates a greater level of the decay of the anti-reflective coating of the one or more lenses of the semiconductor fabrication equipment.

20. The method of claim 18, wherein detecting the photoresist residue comprises measuring the photoresist residue.

* * * * *